United States Patent
Kitahara

(10) Patent No.: US 11,903,758 B2
(45) Date of Patent: Feb. 20, 2024

(54) ULTRASONIC ENDOSCOPE

(71) Applicant: OLYMPUS CORPORATION, Tokyo (JP)

(72) Inventor: Toshihiro Kitahara, Tachikawa (JP)

(73) Assignee: OLYMPUS CORPORATION, Tokyo (JP)

(*) Notice: Subject to any disclaimer, the term of this patent is extended or adjusted under 35 U.S.C. 154(b) by 1216 days.

(21) Appl. No.: 16/261,796

(22) Filed: Jan. 30, 2019

(65) Prior Publication Data

US 2019/0159755 A1 May 30, 2019

Related U.S. Application Data

(63) Continuation of application No. PCT/JP2017/026580, filed on Jul. 21, 2017.

(30) Foreign Application Priority Data

Aug. 4, 2016 (JP) .................................. 2016-153895

(51) Int. Cl.
*A61B 8/12* (2006.01)
*B29C 70/72* (2006.01)
(Continued)

(52) U.S. Cl.
CPC .................. *A61B 8/12* (2013.01); *A61B 8/14* (2013.01); *A61B 8/445* (2013.01); *B29C 64/135* (2017.08);
(Continued)

(58) Field of Classification Search
CPC .................................. A61B 8/12; A61B 8/445
See application file for complete search history.

(56) References Cited

U.S. PATENT DOCUMENTS 5,368,036 A * 11/1994 Tanaka ..................... A61B 8/12
600/104
6,605,043 B1 * 8/2003 Dreschel .............. A61B 8/4483
600/459
(Continued)

FOREIGN PATENT DOCUMENTS

EP 2644103 A1 10/2013
JP H08-256398 A 10/1996
(Continued)

OTHER PUBLICATIONS

International Search Report dated Oct. 17, 2017 issued in PCT/JP2017/026580.
(Continued)

*Primary Examiner* — Oommen Jacob
(74) *Attorney, Agent, or Firm* — Scully, Scott, Murphy & Presser, P.C.

(57) ABSTRACT

A method of manufacturing an ultrasonic transducer module, the ultrasonic transducer module including an ultrasonic transducer, a cable electrically connecting the ultrasonic transducer and a board connectable to an ultrasonic observation device, and a relay board relaying electrical connection between the ultrasonic transducer and the cable, the method including: performing a first molding to form a first part of a casing by molding a single type of resin having an insulation property through a stereo lithographic molding method; and performing a second molding to form a second part of the casing in a state where the ultrasonic transducer, the relay board, and the cable are provided in the first part of the casing, the second part being manufactured by further molding the resin in a side of the first part, in which the ultrasonic transducer, the relay board, and the cable are arranged, through the stereo lithographic molding method.

9 Claims, 10 Drawing Sheets

(51) Int. Cl.
*A61B 8/14* (2006.01)
*A61B 8/00* (2006.01)
*B29L 31/00* (2006.01)
*B33Y 10/00* (2015.01)
*B33Y 80/00* (2015.01)
*B29C 64/135* (2017.01)

(52) U.S. Cl.
CPC .............. *B29C 70/72* (2013.01); *B33Y 10/00* (2014.12); *B33Y 80/00* (2014.12); *B29L 2031/753* (2013.01)

(56) References Cited

U.S. PATENT DOCUMENTS

| | | | | |
|---|---|---|---|---|
| 2013/0158410 | A1* | 6/2013 | Ohgishi | A61B 1/005 600/462 |
| 2013/0204140 | A1 | 8/2013 | Irie | |
| 2014/0058269 | A1* | 2/2014 | Irie | A61B 8/12 600/462 |
| 2015/0148680 | A1* | 5/2015 | Hirayama | A61B 8/4444 600/459 |
| 2015/0276685 | A1 | 10/2015 | Yasuhara et al. | |
| 2015/0282783 | A1 | 10/2015 | Katsura et al. | |
| 2015/0289851 | A1* | 10/2015 | Kobayashi | A61B 8/4494 600/462 |
| 2017/0007213 | A1* | 1/2017 | Motoki | B06B 1/0622 |
| 2017/0143298 | A1 | 5/2017 | Kitahara | |
| 2019/0159755 | A1* | 5/2019 | Kitahara | A61B 8/12 |

FOREIGN PATENT DOCUMENTS

| | | |
|---|---|---|
| JP | 2014-168626 A | 9/2014 |
| WO | WO 2013/077101 A1 | 5/2013 |
| WO | WO 2014/069501 A1 | 5/2014 |
| WO | 2016088496 A1 | 6/2016 |

OTHER PUBLICATIONS

Chinese Office Action dated Jan. 28, 2021 received in 201780047766.7.

* cited by examiner

ULTRASONIC ENDOSCOPE

CROSS-REFERENCE TO RELATED APPLICATION

This application is a continuation of PCT international application Ser. No. PCT/JP2017/026580 filed on Jul. 21, 2017, which designates the United States, incorporated herein by reference, and which claims the benefit of priority from Japanese Patent Application No. 2016-153895, filed on Aug. 4, 2016, incorporated herein by reference.

BACKGROUND

The present disclosure relates to a method of manufacturing an ultrasonic transducer module including an ultrasonic transducer and also relates to an ultrasonic endoscope including an ultrasonic transducer in a distal end of an insertion portion.

In some cases, ultrasonic waves are employed to measure characteristics of a living organism tissue or a material as an observation target in some cases. Specifically, an ultrasonic observation device acquires information regarding characteristics of an observation target by performing a predetermined signal processing for an ultrasonic echo received from an ultrasonic transducer that transmits or receives ultrasonic waves. An ultrasonic endoscope having an ultrasonic transducer in a distal end of an insertion portion is employed to diagnose a living organism tissue in a human body by applying ultrasonic waves.

The ultrasonic transducer has a plurality of piezoelectric elements that convert an electric pulse signal into an ultrasonic pulse (acoustic pulse), irradiate an observation target with the ultrasonic pulse, convert an ultrasonic echo reflected from the observation target to an electric echo signal, and output the electric echo signal. For example, the ultrasonic echo is acquired from the observation target by arranging a plurality of piezoelectric elements along a predetermined direction and electronically switching elements relating the transmit/receive operation.

A plurality of types of ultrasonic transducers are known depending on a transmit/receive direction of the ultrasonic beam, such as a convex type, a linear type, and a radial type. In the convex type ultrasonic transducer, a plurality of piezoelectric elements are arranged along a curved surface, and each piezoelectric element emits the ultrasonic beam toward a radial direction of the curved surface (for example, Publication No. WO 2013/077101 of International Application).

FIG. 16 is a diagram schematically illustrating an exemplary configuration of main parts of a distal end portion of an ultrasonic endoscope having a convex type ultrasonic transducer of the related art. As illustrated in FIG. 16, an ultrasonic transducer module 300 of the related art has an ultrasonic transducer 301, a relay board 302, a cable 303, a board 304, and a casing 305. In this ultrasonic transducer module 300, the ultrasonic transducer 301 is electrically connected to the board 304 provided in a proximal end side of the ultrasonic endoscope through the relay board 302 and the cable 303. Note that the board 304 is electrically connected to the ultrasonic observation device through a cord or the like. When such an ultrasonic transducer module 300 is manufactured, for example, the relay board 302 mounted with the ultrasonic transducer 301 is coupled to a distal end of the cable 303, and the cable 303 is inserted into the casing 305. Then, the board 304 is coupled to the proximal end of the cable 303. Then, the ultrasonic transducer 301 and the relay board 302 are housed in a housing portion 305a of the casing 305, so that the ultrasonic transducer module 300 is manufactured. In this case, the ultrasonic transducer 301 and the relay board 302 are inserted into the housing portion 305a obliquely downward with respect to the insertion direction of the cable 303.

FIG. 17 is a partial cross-sectional view schematically illustrating an exemplary configuration of the distal end portion of the ultrasonic endoscope having the convex type ultrasonic transducer of the related art, in which a plane passing through a longitudinal axis of the distal end portion is set as a cross section. In the ultrasonic endoscope of the related art, a cavity S is formed between the relay board 302 and the housing portion 305a when the ultrasonic transducer 301 is assembled to the casing 305.

SUMMARY

According to one aspect of the present disclosure, a method of manufacturing an ultrasonic transducer module, the ultrasonic transducer module including an ultrasonic transducer, a cable electrically connecting the ultrasonic transducer and a board that is connectable to an ultrasonic observation device, and a relay board relaying electrical connection between the ultrasonic transducer and the cable, the method including: performing a first molding to form a first part of a casing by molding a single type of resin having an insulation property through a stereo lithographic molding method; and performing a second molding to form a second part of the casing in a state where the ultrasonic transducer, the relay board, and the cable are provided in the first part of the casing, the second part being manufactured by further molding the resin in a side of the first part, in which the ultrasonic transducer, the relay board, and the cable are arranged, through the stereo lithographic molding method.

The above and other features, advantages and technical and industrial significance of this invention will be better understood by reading the following detailed description of presently preferred embodiments of the disclosure, when considered in connection with the accompanying drawings.

DETAILED DESCRIPTION

Figure 1:
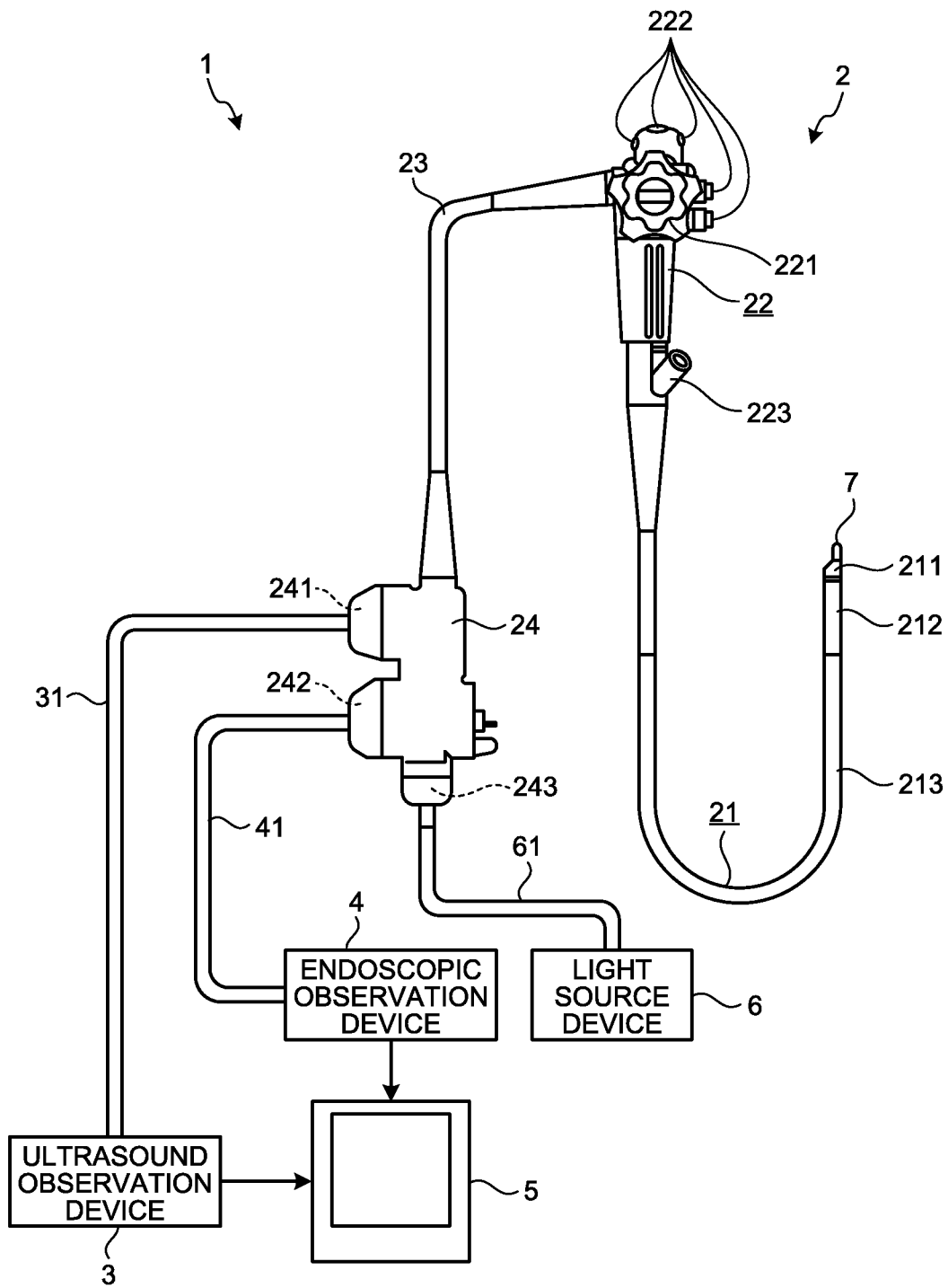
FIG. 1 is a diagram schematically illustrating an endoscope system according to an embodiment of the present disclosure.

Hereinafter, modes for carrying out the disclosure (hereinafter, referred to as an embodiment) will be described with reference to the accompanying drawings. Note that the disclosure is not limited by the embodiments described below. In addition, like reference numerals denote like elements throughout the drawings.

Embodiments

FIG. 1 is a diagram schematically illustrating an endoscope system according to the embodiment. An endoscope system 1 is a system for performing an ultrasonic diagnosis for a subject such as a human being using an ultrasonic endoscope. The endoscope system 1 has an ultrasonic endoscope 2, an ultrasonic observation device 3, an endoscopic observation device 4, a display device 5, and a light source device 6 as illustrated in FIG. 1.

The ultrasonic endoscope 2 has a distal end portion that converts an electric pulse signal received from the ultrasonic observation device 3 into an ultrasonic pulse (acoustic pulse), irradiates the subject with the ultrasonic pulse, converts the ultrasonic echo reflected from the subject into an electric echo signal that expresses the ultrasonic echo as a voltage change, and outputs the electric echo signal.

The ultrasonic endoscope 2 has an imaging optical system and an image sensor and is inserted into a digestive tract (such as esophagus, stomach, duodenum, and large intestine) or a respiratory organ (such as trachea or bronchus) of the subject to capture the digestive tract or the respiratory organs. In addition, the ultrasonic endoscope 2 can capture surrounding organs (such as pancreas, gallbladder, bile duct, biliary tract, lymph node, mediastinum, or blood vessels) using ultrasonic waves. Furthermore, the ultrasonic endoscope 2 has a light guide that guides illumination light with which the subject is irradiated during optical capturing. The light guide has a distal end portion reaching a distal end of the insertion portion of the ultrasonic endoscope 2 inserted into the subject and a proximal end portion coupled to a light source device 6 that generates the illumination light.

As illustrated in FIG. 1, the ultrasonic endoscope 2 has an insertion portion 21, a manipulation portion 22, a universal cord 23, and a connector 24. The insertion portion 21 is a portion inserted into the subject. As illustrated in FIG. 1, the insertion portion 21 has a hard distal end portion 211 provided in a distal end side to hold an ultrasonic transducer 7, a curved portion 212 connected to the proximal end side of the distal end portion 211 to be curved, and a flexible pipe portion 213 connected to the proximal end side of the curved portion 212 with flexibility. Here, although not illustrated in details, the insertion portion 21 is internally provided with a light guide that transmits illumination light supplied from the light source device 6 and a surgical tool insertion passage for guiding a plurality of signal cables for transmitting various signals and inserting a surgical tool. Note that, in this specification, the ultrasonic transducer 7 side of the insertion portion 21 is set as the distal end side, and the side linked to the manipulation portion 22 is set as the proximal end side.

The ultrasonic transducer 7 may be any one of a convex transducer or a linear transducer. According to the embodiment, it is described that the ultrasonic endoscope 2 has a plurality of piezoelectric elements arranged in an array shape as the ultrasonic transducer 7, and performs electronic scanning by switching the piezoelectric elements relating to transmit/receive operations or delaying the transmit/receive operations of each piezoelectric element in an electronic manner. However, the ultrasonic transducer 7 may perform scanning in a mechanical manner. A configuration of the ultrasonic transducer 7 will be described below.

Figure 2:
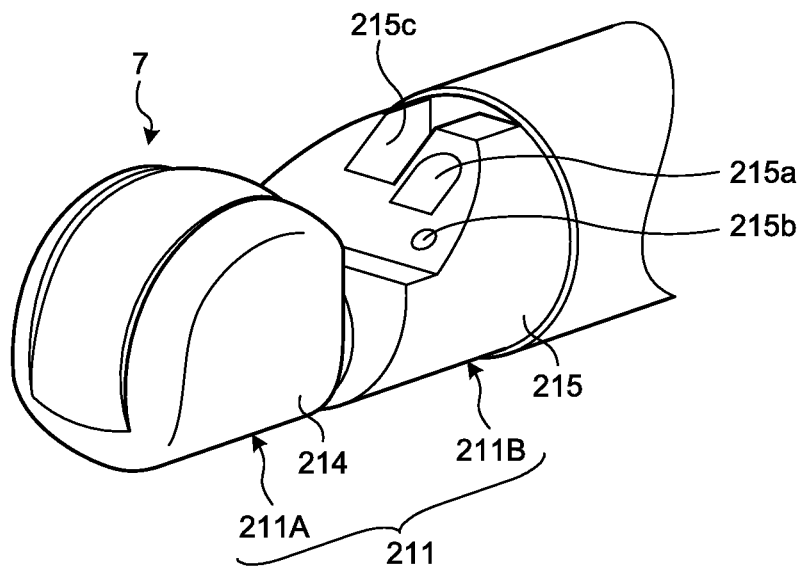
FIG. 2 is a perspective view schematically illustrating a configuration of a distal end of an insertion portion of the ultrasonic endoscope according to the embodiment.
Figure 3:
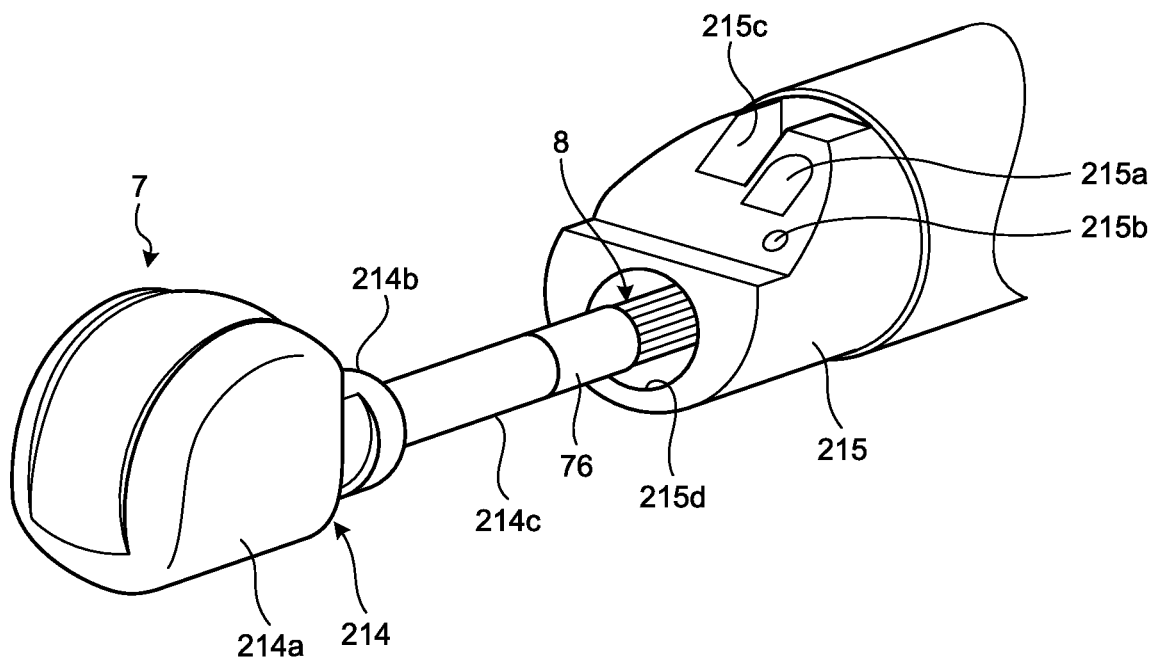
FIG. 3 is an exploded perspective view schematically illustrating a configuration of a distal end of the insertion portion of the ultrasonic endoscope according to the embodiment.

FIG. 2 is a perspective view schematically illustrating a configuration of the distal end of the insertion portion of the ultrasonic endoscope according to the embodiment. FIG. 3 is an exploded perspective view schematically illustrating the configuration of the distal end of the insertion portion of the ultrasonic endoscope according to the embodiment. As illustrated in FIG. 2, the distal end portion 211 has an ultrasonic function portion 211A provided with the ultrasonic transducer 7, and an endoscopic function portion 211B provided with a second casing 215 having an observation window 215a used to allow light to be incident to an imaging optical system having an objective lens or the like that receives light from the outside and an illumination window 215b as a part of an illumination optical system that condenses the illumination light and emits it to the outside. The second casing 215 has a surgical tool protruding port 215c formed to communicate with the surgical tool insertion passage of the insertion portion 21 and allow a surgical tool to protrude from the distal end of the insertion portion 21. The endoscopic function portion 211B has one end detachably coupled to the ultrasonic function portion 211A and the other end coupled to the curved portion 212. The surgical tool insertion passage is provided such that a vicinity of the end linked to the surgical tool protruding port 215c is inclined with respect to a longitudinal axis of the insertion portion 21, and the surgical tool protrudes from the surgical tool protruding port 215c in a direction inclined from the longitudinal axis. Here, the "longitudinal axis" refers to an axis along the longitudinal direction of the insertion portion 21. An axial direction of the curved portion 212 or the flexible pipe portion 213 changes depending on each position. However, the hard distal end portion 211 has a longitudinal axis which is a constant straight axis.

The manipulation portion 22 is a portion connected to the proximal end side of the insertion portion 21 to receive various manipulations from a doctor or the like. As illustrated in FIG. 1, the manipulation portion 22 has a curving knob 221 for manipulating a curve operation of the curved portion 212 and a plurality of manipulation members 222 for performing various manipulations. In addition, the manipulation portion 22 has a surgical tool insertion port 223 communicating with the surgical tool insertion passage to insert the surgical tool to the surgical tool insertion passage.

The universal cord 23 extends from the manipulation portion 22 and includes the plurality of signal cables for transmitting various signals, optical fibers for transmitting the illumination light supplied from the light source device 6, or the like.

The connector 24 is provided in a distal end of the universal cord 23. In addition, the connector 24 has first to third connector portions 241 to 243 coupled to an ultrasonic cable 31, a video cable 41, and an optical fiber cable 61, respectively.

The ultrasonic observation device 3 is electrically coupled to the ultrasonic endoscope 2 through the ultrasonic cable 31 (refer to FIG. 1) to output a pulse signal to the ultrasonic endoscope 2 through the ultrasonic cable 31 and receives an echo signal from the ultrasonic endoscope 2. In addition, the ultrasonic observation device 3 creates an ultrasonic image by applying a predetermined processing to the echo signal.

The endoscopic observation device 4 is electrically coupled to the ultrasonic endoscope 2 through the video cable 41 (refer to FIG. 1) to receive an image signal from the ultrasonic endoscope 2 through the video cable 41. In addition, the endoscopic observation device 4 creates an endoscopic image by applying a predetermined processing to the image signal.

The display device 5 includes a liquid crystal or organic electro luminescence (EL) projector, a cathode ray tube (CRT), or the like to display the ultrasonic image created by the ultrasonic observation device 3 or the endoscopic image created by the endoscopic observation device 4.

The light source device 6 is coupled to the ultrasonic endoscope 2 through the optical fiber cable 61 (refer to FIG. 1) to supply illumination light for illuminating the inside of the subject to the ultrasonic endoscope 2 through the optical fiber cable 61.

Figure 4:
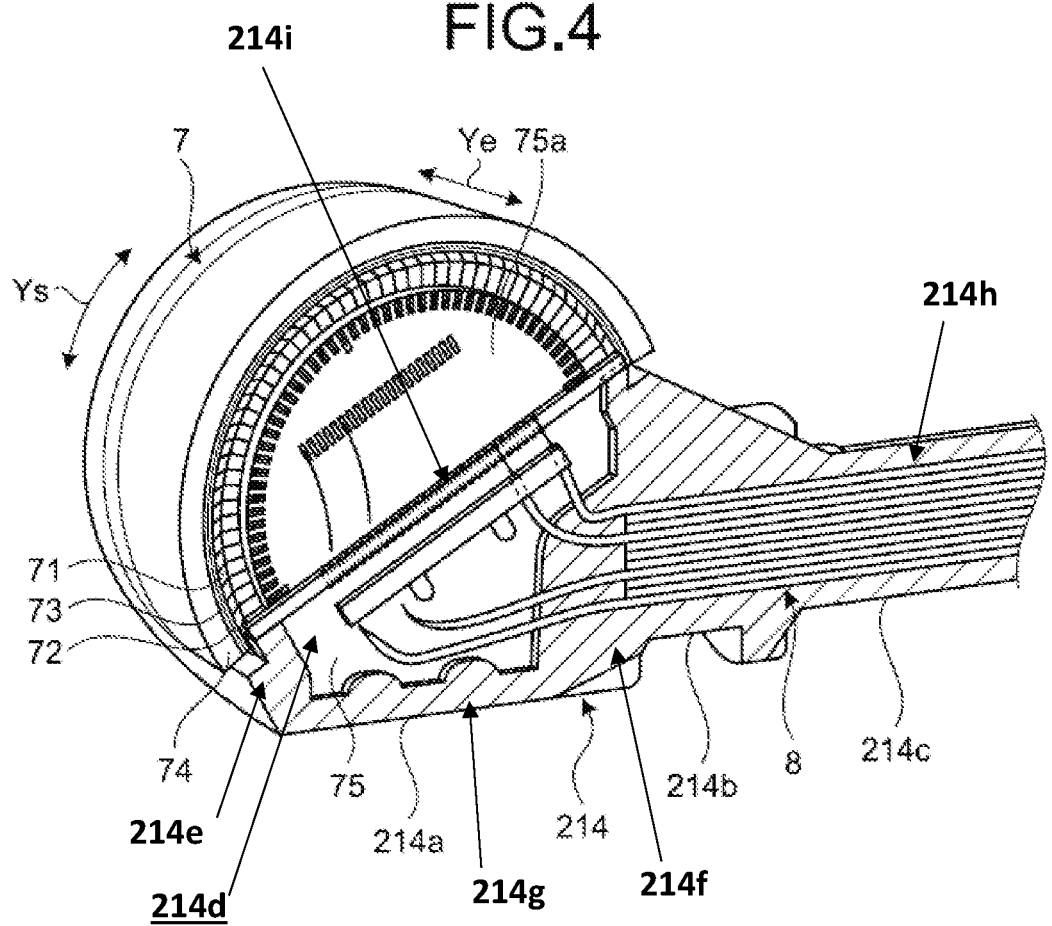
FIG. 4 is a partial cross-sectional view schematically illustrating a configuration of an ultrasonic function portion according to the embodiment.
Figure 5:
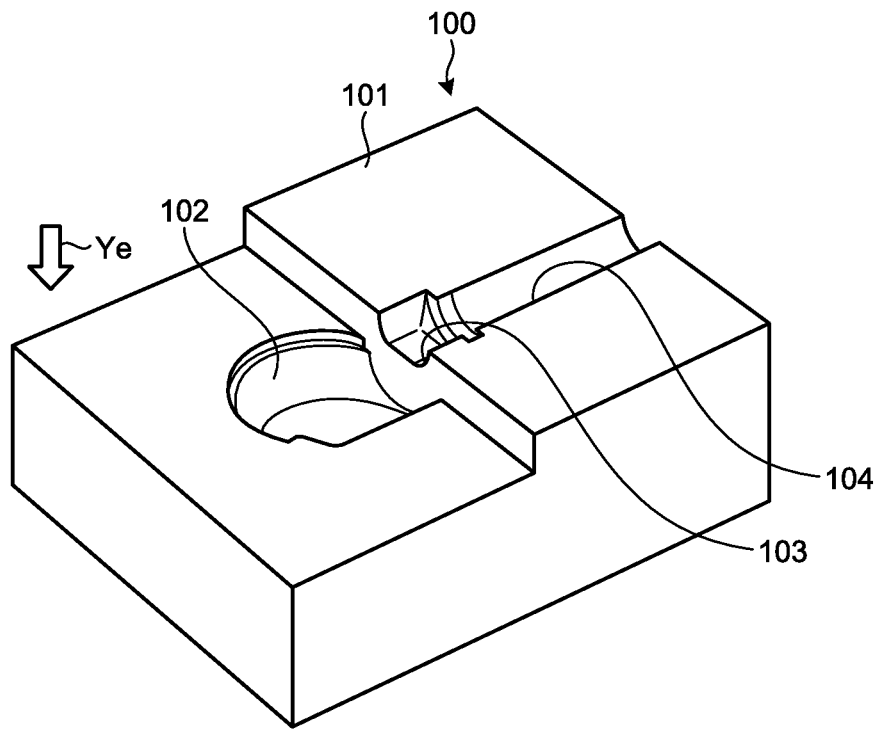
FIG. 5 is a diagram illustrating a method of manufacturing an ultrasonic transducer module according to the embodiment.

Subsequently, the configuration of the ultrasonic transducer 7 provided in the distal end of the insertion portion 21 will be described with reference FIGS. 2 to 4. FIG. 4 is a partial cross-sectional view schematically illustrating a configuration of the ultrasonic function portion according to the embodiment, in which a plane passing through the longitudinal axis of the insertion portion 21 is set as a cross section. In the embodiment, it is described that the ultrasonic transducer 7 is a convex type ultrasonic transducer as illustrated in FIG. 2 and has a one-dimensional array (1D array) shape where a plurality of piezoelectric elements 71 are arranged in line. In other words, in the ultrasonic transducer 7 according to the embodiment, a plurality of piezoelectric elements 71 are arranged along an outer surface of the curved surface of the ultrasonic transducer 7 including the longitudinal axis, and ultrasonic waves are transmitted/received on a scanning surface parallel with the longitudinal axis.

The ultrasonic transducer 7 has a plurality of piezoelectric elements 71, which has a square pillar shape and are aligned along the longitudinal direction, first and second acoustic matching layers 72 and 73 respectively provided on an outer surface side of the ultrasonic transducer 7 with respect to each piezoelectric element 71, an acoustic lens 74 provided oppositely to a side adjoining the piezoelectric elements 71 of the second acoustic matching layer 73, a relay board 75 used to electrically couple cables inserted into each piezoelectric element 71 and the insertion portion 21, and a backing member (not illustrated) provided oppositely to a side adjoining the first acoustic matching layer 72 of the piezoelectric element 71. The backing member is filled in a hollow space formed between the piezoelectric element 71 and a wall portion having a cup shape to house a part of the relay board 75. The relay board 75 is electrically coupled to each piezoelectric element 71 through a flexible board 75a and is coupled to a cable group 8 including a plurality of cables inserted into the insertion portion 21.

The piezoelectric element 71 converts an electric pulse signal into an ultrasonic pulse (acoustic pulse), irradiates the subject with the ultrasonic pulse, receives an ultrasonic echo reflected from the subject, converts the ultrasonic echo into an electric echo signal expressing a voltage change, and outputs the electric echo signal. Hereinafter, an "elevation direction Ye" refers to a longitudinal direction of the piezoelectric element 71 perpendicular to the scan surface of the ultrasonic transducer 7, and a "scan direction Ys" refers to an arrangement direction of the piezoelectric elements 71.

The first and second acoustic matching layers 72 and 73 perform acoustic impedance matching between the piezoelectric element 71 and the observation target in order to effectively transmit sound (ultrasonic waves) between the piezoelectric element 71 and the observation target. The first and second acoustic matching layers 72 and 73 may include a plurality of layers formed of different materials in each layer or may include any one of the layers depending on characteristics of the piezoelectric element 71 and the observation target.

The acoustic lens 74 covers the second acoustic matching layer 73 and the outer surface of the wall portion. The acoustic lens 74 forms a part of the outer surface of the ultrasonic transducer 7. The acoustic lens 74 is formed of silicon, polymethylpentene, epoxy resin, polyetherimide, or the like and has one surface having a convex shape or concave shape to serve as a diaphragm for ultrasonic waves, so that the ultrasonic wave passing through the second acoustic matching layer 73 is emitted to the outside, or an ultrasonic echo is received from the outside. The acoustic lens 74 transmits or receives ultrasonic waves in a part that covers the second acoustic matching layer 73, and a surface of this part serves as an ultrasonic wave transmit/receive surface.

The backing member attenuates unnecessary ultrasonic vibration caused by the operation of the piezoelectric element 71. The backing member is formed of a material having a large attenuation factor, for example, including epoxy resin in which a filler such as alumina or zirconia is dispersed, or rubber in which the aforementioned filler is dispersed.

The ultrasonic function portion 211A is formed of a single type of resin having an insulation property and is detachably coupled to the endoscopic function portion 211B as described above. Specifically, the ultrasonic function portion 211A has an ultrasonic transducer 7 and a first casing 214 that holds the ultrasonic transducer 7. The first casing 214 has a main body portion 214a that holds the ultrasonic transducer 7. The first casing 214 has a first opening 214i defining a cavity 214d, where the cavity 214d has at least a distal wall 214e, a proximal wall 214f and a bottom wall 214g, an ultrasonic wave transmission/reception surface of the ultrasonic transducer 7 is exposed from the first opening 214i and the relay board 75 is disposed from the cavity 214d. The first casing 214 also having a coupling portion 214b that protrudes from the main body portion 214a and is coupled to the endoscopic function portion 211B, and an extension portion 214c extending from an end of the side opposite to the main body portion 214a of the coupling portion 214b, the extension portion 214c having a second opening 214h piercing the proximal wall 214f of the first casing 214 on a proximal side of the first casing 214 for accommodating the cable 8. In comparison, the second casing 215 of the endoscopic function portion 211B has a hole portion 215d provided in an end of a side opposite to the side coupled to the curved portion 212 and is coupled to the first casing 214. The ultrasonic function portion 211A and the endoscopic function portion 211B are coupled by fitting the coupling portion 214b to the hole portion 215d. In this case, the ultrasonic function portion 211A and the endoscopic function portion 211B may be fixed using a method known in the art, such as an adhesive or screws. Note that the first casing 214 may have a groove or protrusion capable of engaging a balloon (not illustrated). In addition, the first casing 214 may be formed of a plurality of types of resin as long as they have an insulation property.

In addition, an extension part of the cable group 8 from the ultrasonic function portion 211A has a binding band 76 that binds each cable of the cable group 8.

In the ultrasonic transducer 7 having the aforementioned configuration, each piezoelectric element 71 vibrates in response to an input of the pulse signal, so that the observation target is irradiated with ultrasonic waves through the first acoustic matching layer 72, the second acoustic matching layer 73, and the acoustic lens 74. In this case, vibration of the piezoelectric element 71 is attenuated by the backing member in a side of the piezoelectric element 71 opposite to the side where the first acoustic matching layer 72, the second acoustic matching layer 73, and the acoustic lens 74 are arranged, so that the vibration of the piezoelectric element 71 is not transmitted. In addition, the ultrasonic wave reflected from the observation target is transmitted to the piezoelectric element 71 through the first acoustic matching layer 72, the second acoustic matching layer 73, and the acoustic lens 74. The piezoelectric element 71 is vibrated by the transmitted ultrasonic wave so as to convert this vibration into an echo signal. The echo signal is output to the ultrasonic observation device 3 through the cable group 8 or the like.

Subsequently, a method of manufacturing the ultrasonic transducer module having the first casing 214, the ultrasonic transducer 7, and the cable group 8 will be described with reference to FIGS. 5 to 13. FIGS. 5 to 13 are diagrams illustrating a method of manufacturing the ultrasonic transducer module according to the embodiment. In this manufacturing method, the first casing 214 is molded by discharging resin to a die 100 of FIG. 5 on the basis of a preset program, for example, using a 3D printer. The manufacturing of the molding by discharging resin is performed on the basis of a layered shaping method in which resin is layered in a designed shape by discharging the resin heated over a melting point and solidifying it. As a result, an ultrasonic transducer module is manufactured, in which the first casing 214 holds the ultrasonic transducer 7, and the cable group 8 extends from the first casing 214. The ultrasonic transducer module according to the embodiment at least has an ultrasonic transducer 7, a cable group 8, a relay board 75, and a first casing 214. The resin is discharged along the elevation direction Ye of the piezoelectric element 71 when the first casing 214 holds the ultrasonic transducer 7. Alternatively, without limiting to the layered shaping method, other stereo lithographic molding methods such as laser beam lithography or a powder method may be employed.

The die 100 includes a mold member 101 having a stepped erecting shape. The mold member 101 has a first mold portion 102 that assists molding of the main body portion 214a, a second mold portion 103 that assists molding of the coupling portion 214b, and a third mold portion 104 that assists molding of the extension portion 214c. All of the first, second, and third mold portions 102, 103, and 104 have a hole shape matching a shape of an outer surface of a molding target portion of the first casing 214.

Figure 6:
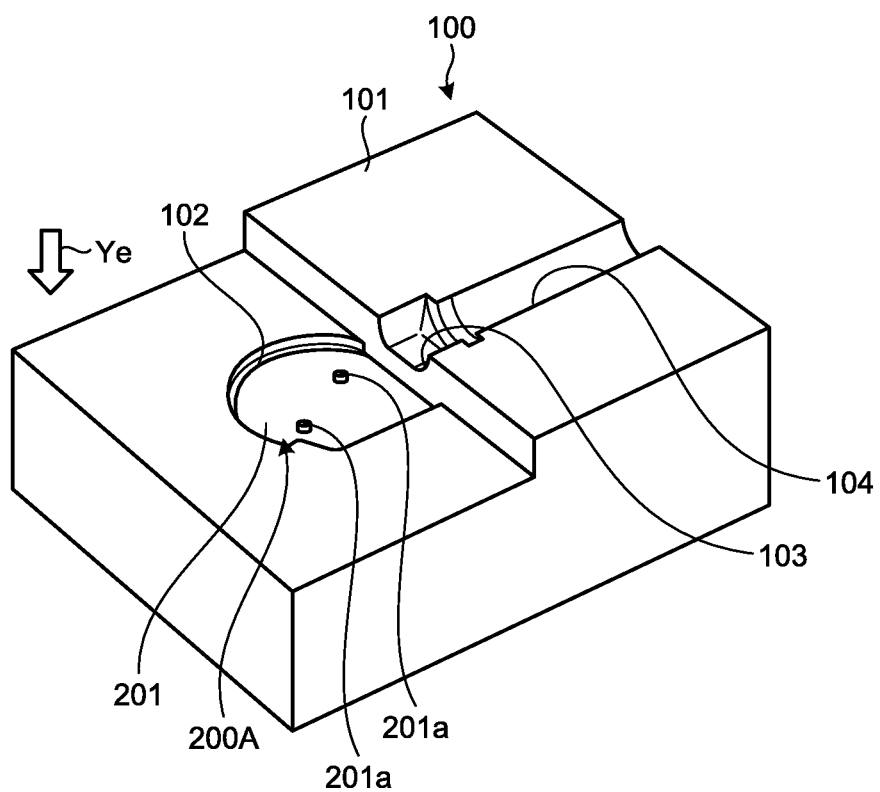
FIG. 6 is a diagram illustrating a method of manufacturing an ultrasonic transducer module according to the embodiment.

First, a first molding 200A as a part of the main body portion 214a including a side portion 201 that holds one side surface of the ultrasonic transducer 7 is molded by discharging resin to the first mold portion 102 (refer to FIG. 6). A pair of protrusions 201a is molded on a top surface of the side portion 201. The protrusion 201a is housed in a concave portion 74a formed on the side surface of the acoustic lens 74 (refer to FIG. 9) and has a function of positioning the main body portion 214a and the ultrasonic transducer 7. The concave portion 74a has a hole shape that forms a pillar-shaped space extending along the elevation direction Ye.

Figure 7:
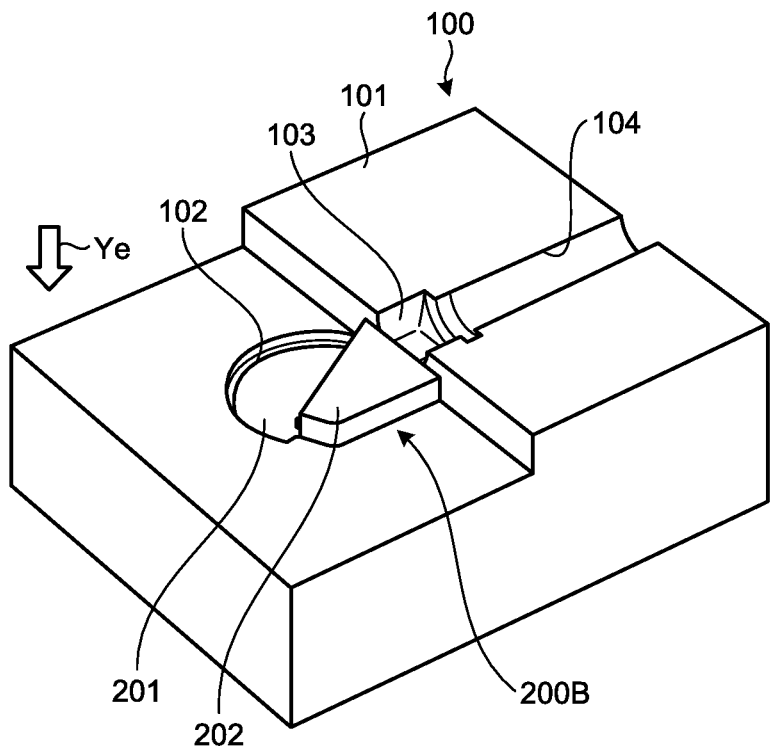
FIG. 7 is a diagram illustrating a method of manufacturing an ultrasonic transducer module according to the embodiment.

After the first molding 200A is molded, a second molding 200B is molded by further molding a placing portion 202 that serves as a placing surface of the relay board 75 by continuously discharging resin to the first mold portion 102 on the basis of the program (refer to FIG. 7).

Figure 8:
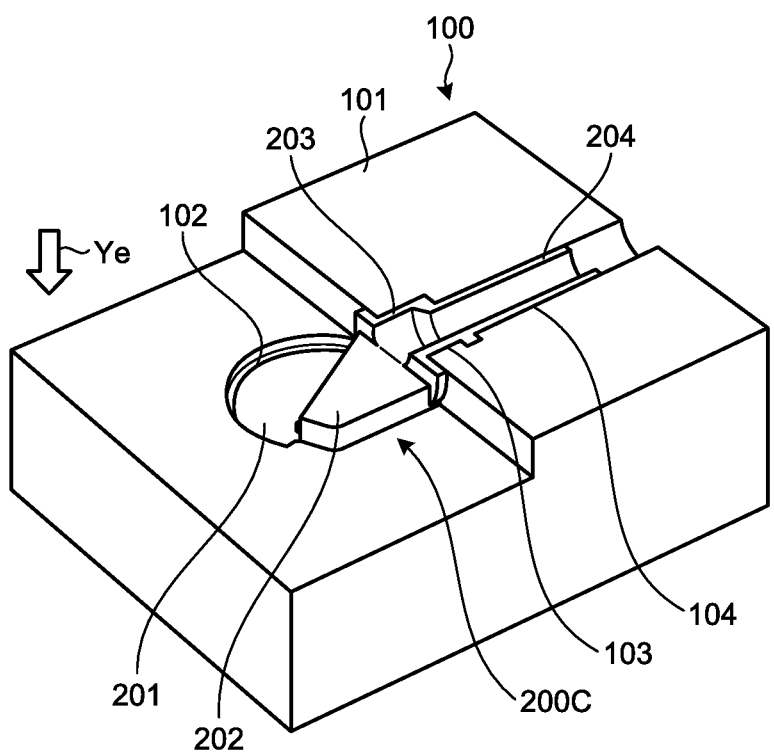
FIG. 8 is a diagram illustrating a method of manufacturing an ultrasonic transducer module according to the embodiment.

After the second molding 200B is molded, a third molding 200C is molded by further molding a partial coupling portion 203 which is a part of the coupling portion 214b and a partial extension portion 204 which is a part of the extension portion 214c by continuously discharging resin to the second and third mold portions 103 and 104 (refer to FIG. 8). The partial coupling portion 203 corresponds to, for example, one of two parts obtained by bisecting the coupling portion 214b. Similarly, the partial extension portion 204 corresponds to, for example, one of two parts obtained by bisecting the extension portion 214c. Through the molding processing described above, substantially a half of the first casing 214 is formed (first molding step). Here, the "half" refers to a molding corresponding to one of sections obtained by dividing the first casing 214 on a plane parallel with the ultrasonic wave transmission direction, including a case where a volume of one of the moldings is different from a volume of the other molding. The molding formed by the first molding step is not necessarily bisected on a plane passing through the center axis of the first casing 214. Instead, any other method may be employed as long as the first casing 214 can be molded in a case where resin is discharged from one side, and the resin is then discharged from the other side.

Figure 9:
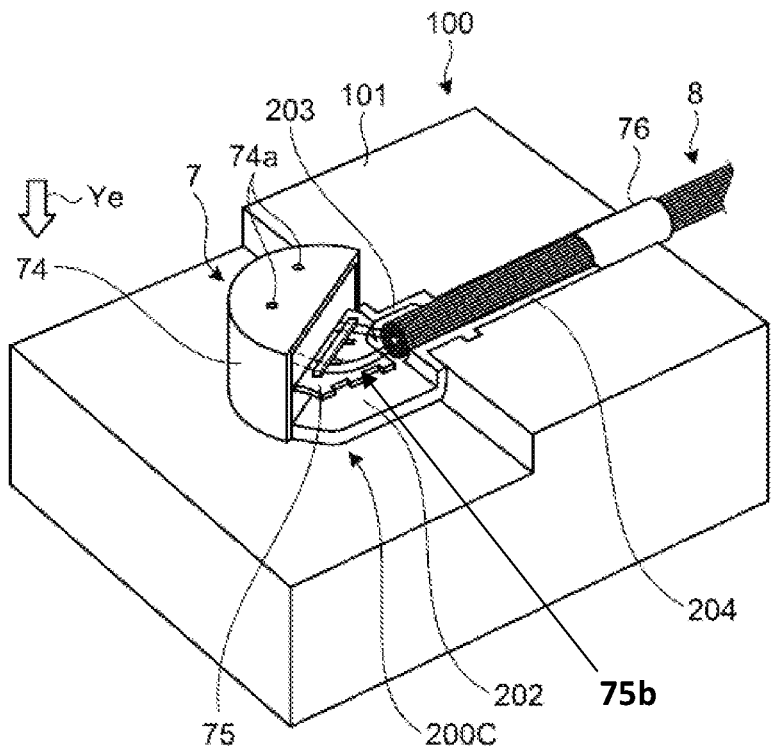
FIG. 9 is a diagram illustrating a method of manufacturing an ultrasonic transducer module according to the embodiment.
Figure 10:
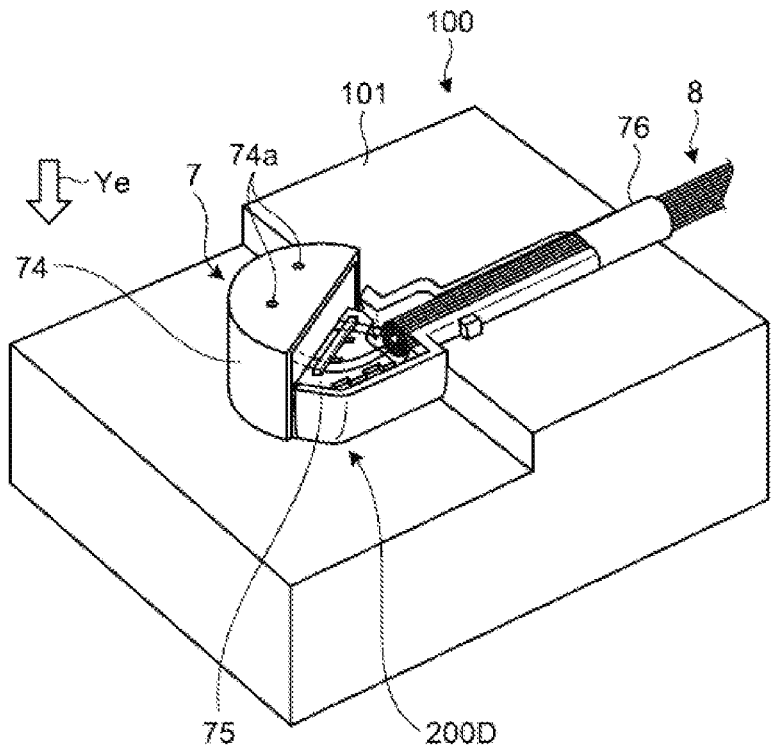
FIG. 10 is a diagram illustrating a method of manufacturing an ultrasonic transducer module according to the embodiment.
Figure 11:
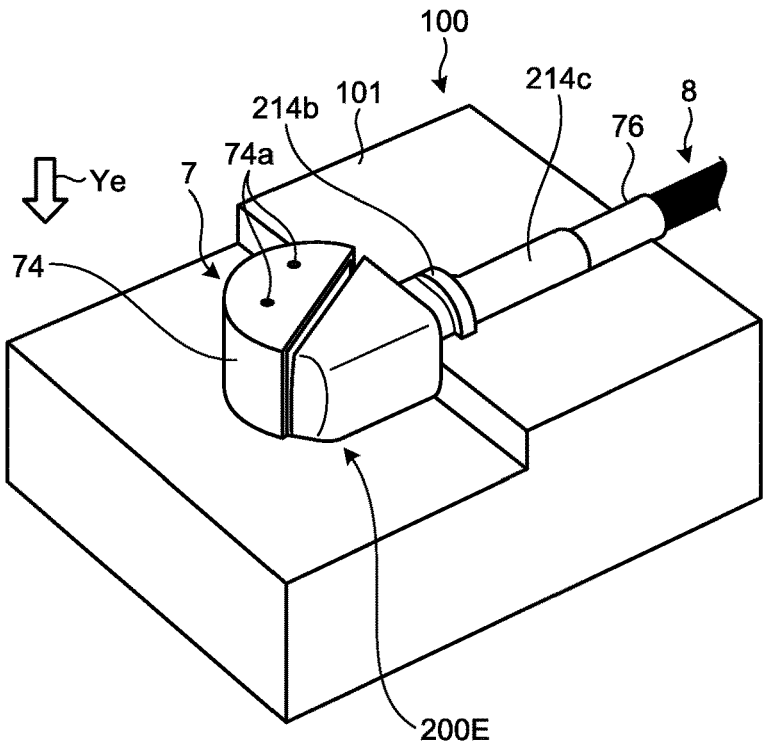
FIG. 11 is a diagram illustrating a method of manufacturing an ultrasonic transducer module according to the embodiment.

Then, the ultrasonic transducer 7, the relay board 75, and the cable group 8 are placed on the third molding 200C (refer to FIG. 9). The ultrasonic transducer 7, the relay board 75, and the cable group 8 are assembled in advance. In this case, the acoustic lens 74 of the ultrasonic transducer 7 has a pair of concave portions 74a formed on both side surfaces of the elevation direction Ye. When the ultrasonic transducer 7 is placed on the third molding 200C, the aforementioned protrusion 201a is housed in the concave portion 74a formed on one of the side surfaces so as to position the ultrasonic transducer 7 and the third molding 200C. Incidentally, a part of the ultrasonic transducer 7, the relay board 75, and the cable group 8 may be assembled on the die 100.

The discharging of resin starts again while the ultrasonic transducer 7, the relay board 75, and the cable group 8 are placed on the third molding 200C. A fourth molding 200D is obtained by further layering an outer peripheral portion of the first casing 214 (refer to FIG. 10). A fifth molding 200E is obtained by molding the coupling portion 214b and the extension portion 214c while the relay board 75 is covered by the resin (refer to FIG. 11).

Figure 12:
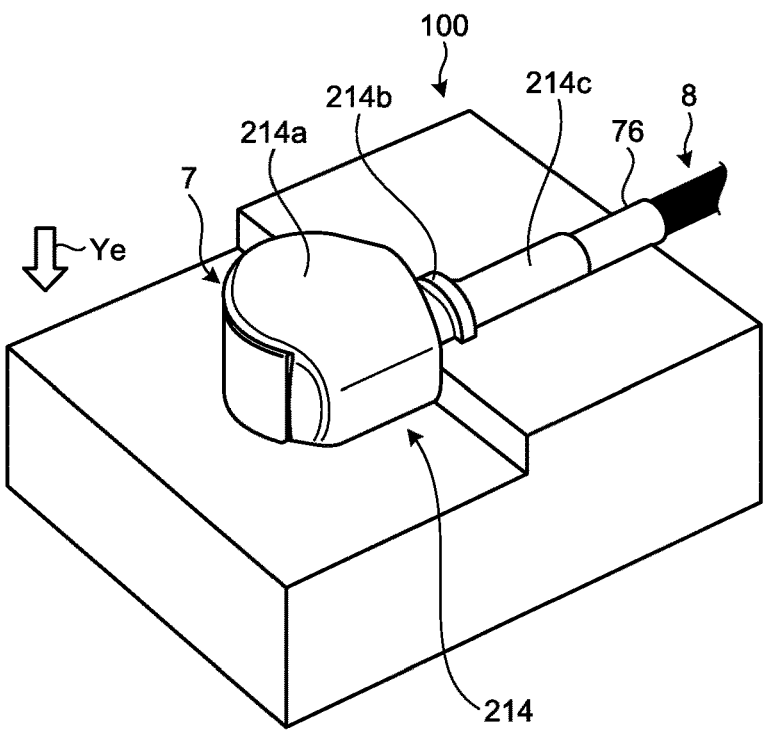
FIG. 12 is a diagram illustrating a method of manufacturing an ultrasonic transducer module according to the embodiment.

Then, the main body portion 214a is molded by further continuously discharging the resin, so as to manufacture the first casing 214 in which the ultrasonic transducer 7 or the relay board 75 are held, and the cable group 8 is inserted (second molding step: refer to FIG. 12). In this case, the resin is filled in the other concave portion 74a illustrated in FIG. 9 or the like, so that the ultrasonic transducer 7 and the main body portion 214a are also positioned on the other side surface.

Figure 13:
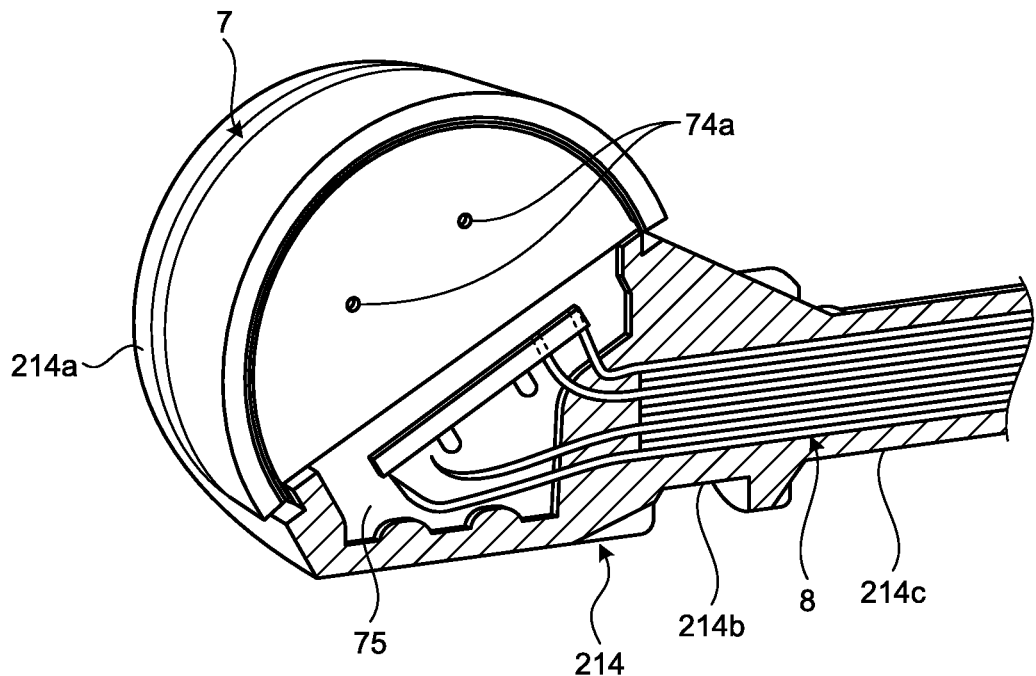
FIG. 13 is a diagram illustrating a method of manufacturing an ultrasonic transducer module according to the embodiment.
Figure 17:
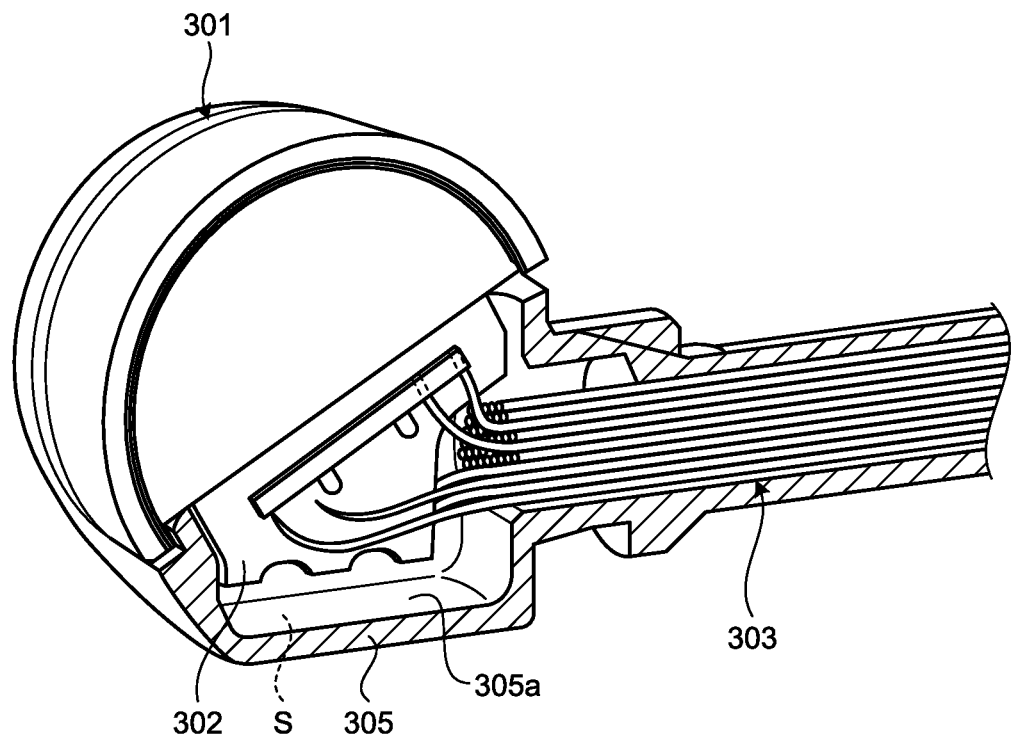
FIG. 17 is a partial cross-sectional view schematically illustrating an exemplary configuration of the distal end portion of the ultrasonic endoscope having the convex type ultrasonic transducer of the related art, in which a plane passing through a longitudinal axis of the distal end portion is set as a cross section.

The main body portion 214a manufactured through the aforementioned molding processing does not have the cavity S illustrated in FIG. 17 because at least the bottom wall 214g of the cavity 214d that opposes the opening 214i abuts on at least one side (edge) 75b (see FIG. 9) of the relay board 75 or the main body portion 214a abuts the cable group 8 as illustrated in FIG. 13.

According to the embodiment described above, it is possible to reduce the size of the first casing 214 as much as the cavity that has been formed in the related art by molding the first casing 214 on the basis of a stereo lithographic molding method. In the manufacturing method according to the embodiment described above, a work necessary for assembling the ultrasonic transducer 7, the relay board 75, and the cable group 8 with the first casing 214 is performed merely by placing them, and the first casing 214 can be manufactured without forming a cavity for inserting the cable group 8 or the relay board 75 unlike the work of the related art. For this reason, it is possible to achieve miniaturization by removing necessity of providing the cavity in the casing. In addition, the first casing 214 molded in this manner can abut on the ultrasonic transducer 7, the relay board 75, and the cable group 8. In addition, it is possible to suppress the ultrasonic transducer 7 or the like from being deviated with respect to the first casing 214 by an external load.

In addition, since the resin is discharged along the elevation direction Ye according to the aforementioned embodiment, it is possible to manufacture the first casing 214 for holding the ultrasonic transducer 7 using a single die 100 without rotating or inverting the die 100 or the molding.

Note that, although the aforementioned embodiment has been described by assuming that the resin is discharged along the elevation direction Ye in the event of the stereo lithographic molding, the resin may be discharged in a direction different from the elevation direction Ye as long as the first casing 214 can be molded.

In addition, although the aforementioned embodiment has been described by assuming that the molding is molded to match the shape of the mold portion formed in the die 100, the first casing 214 may be manufactured by molding the other side portion 201 by discharging resin to an assembly of the ultrasonic transducer 7, the relay board 75, and the cable group 8 along the elevation direction Ye to mold one of the side portions 201 of the first casing 214, and then discharging resin by inverting the molding including the ultrasonic transducer 7, the relay board 75, and the cable group 8.

In addition, although the aforementioned embodiment has been described by assuming that the concave portion 74a for positioning with the main body portion 214a forms a pillar-shaped space extending in the elevation direction Ye, the shape of the concave portion 74a is not limited thereto as long as the main body portion 214a and the ultrasonic transducer 7 can be positioned. For example, the protrusion may be formed in the acoustic lens 74 side, and the concave portion may be formed in the main body portion 214a side. In addition, the concave portion may have a trench shape extending on the surface of the acoustic lens 74. Hereinafter, an exemplary modification of the ultrasonic transducer will be described with reference to FIGS. 14 and 15.

First Modification of Embodiment

Figure 14:
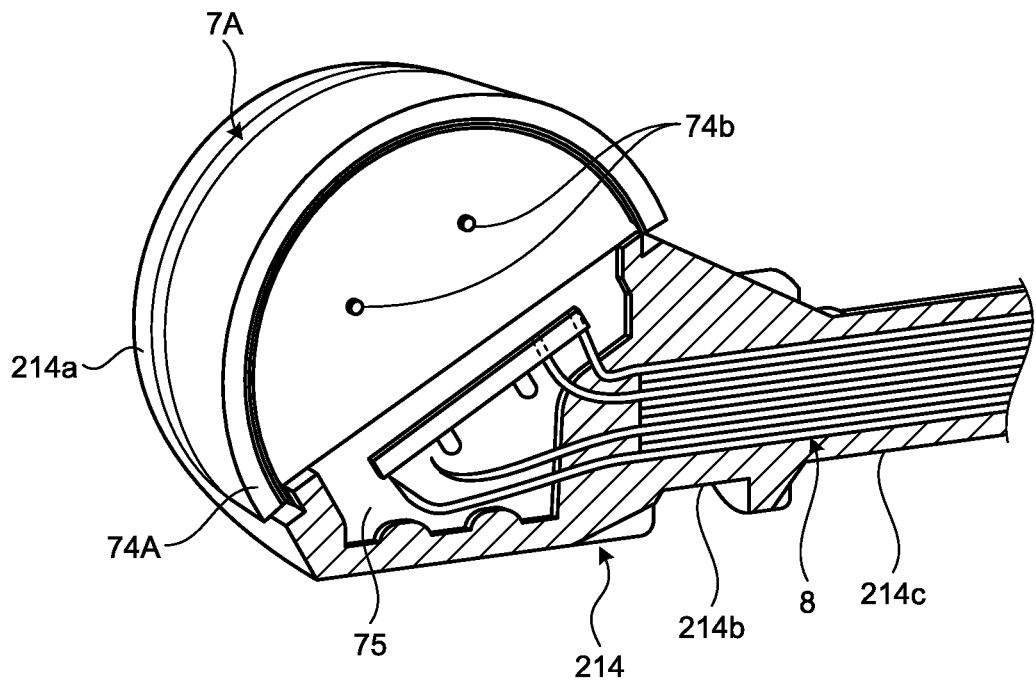
FIG. 14 is a partial cross-sectional view schematically illustrating an exemplary configuration of a distal end portion of an ultrasonic endoscope according to a first modification of the embodiment, in which a plane passing through a longitudinal axis of the distal end portion is set as a cross section.

FIG. 14 is a partial cross-sectional view schematically illustrating an exemplary configuration of a distal end portion of an ultrasonic endoscope according to a first modification of the embodiment, in which a plane passing through the longitudinal axis of the distal end portion is set as a cross section. An ultrasonic transducer 7A according to the first modification has an acoustic lens 74A instead of the acoustic lens 74 of the ultrasonic transducer 7 described above. The acoustic lens 74A has a protrusion 74b protruding from the surface of the acoustic lens 74A. In this case, a concave portion having a concave shape matching the protrusion 74b is formed in the main body portion 214a. As this protrusion 74b is housed in the concave portion, the main body portion 214a and the ultrasonic transducer 7A are positioned.

Second Modification of Embodiment

Figure 15:
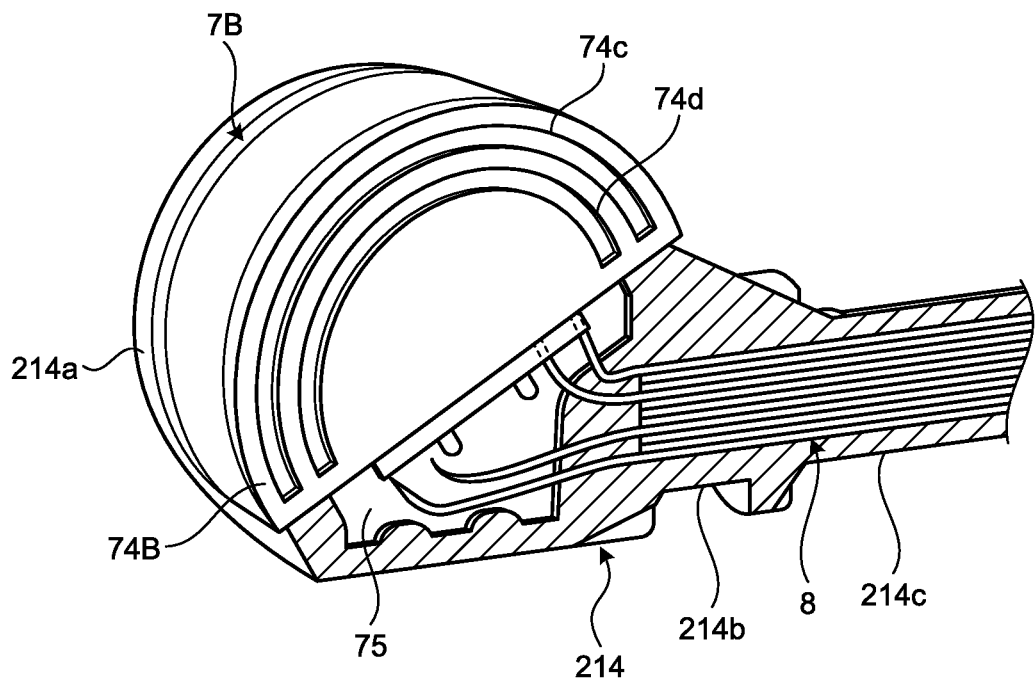
FIG. 15 is a partial cross-sectional view schematically illustrating an exemplary configuration of a distal end portion of an ultrasonic endoscope according to a second modification of the embodiment, in which a plane passing through a longitudinal axis of the distal end portion is set as a cross section.
Figure 16:
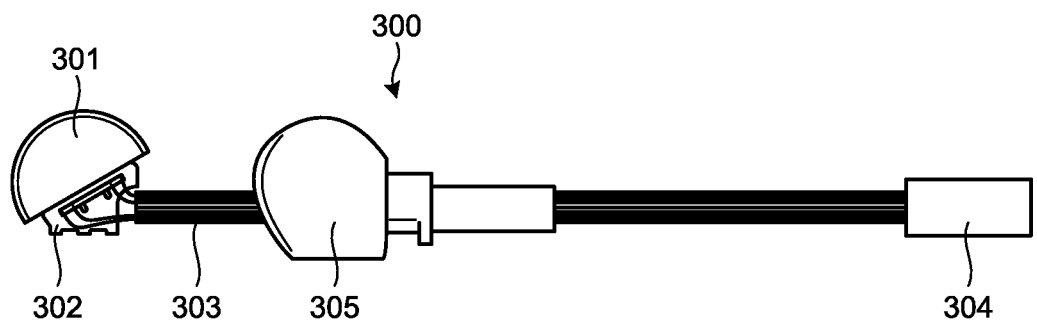
FIG. 16 is diagram schematically illustrating exemplary configurations of main parts of a distal end portion of the ultrasonic endoscope having a convex type ultrasonic transducer of the related art.

FIG. 15 is a partial cross-sectional view schematically illustrating an exemplary configuration of a distal end portion of an ultrasonic endoscope according to a second modification of the embodiment, in which a plane passing through the longitudinal axis of the distal end portion is set as a cross section. An ultrasonic transducer 7B according to the second modification has an acoustic lens 74B instead of the acoustic lens 74 of the ultrasonic transducer 7 described above. The acoustic lens 74B has a pair of concave portions 74c and 74d having a trench shape extending in an arc shape on a surface of the acoustic lens 74B. In this case, the main body portion 214a has a protrusion protruding to match the concave portions 74c and 74d. As this protrusion is housed in the concave portions 74c and 74d, the main body portion 214a and the ultrasonic transducer 7B are positioned.

Note that, in the modifications described above, the concave portion may be formed in any one of the concave portions 74c and 74d, or the concave portions provided in the opposite side surfaces may be different. For example, the concave portion 74c may be formed in one of the side surfaces, and the concave portion 74d may be formed in the other side surface.

While modes for carrying out the disclosure have been described hereinbefore, the disclosure is not limited by the embodiments and modifications described above. The disclosure is not limited to the embodiments and modifications described above and can encompass various embodiments without departing from the spirit and scope of the disclosure described in claims. In addition, the configurations of the embodiments and modifications may be combined appropriately.

Note that, although the 1D array has been described by way of example in the aforementioned embodiments, the disclosure can be applied to a 1.25D, 1.5D, or 1.75D array, or the like in which a plurality of piezoelectric elements (oscillation portion) are arranged in the direction (the elevation direction) substantially perpendicular to the scan direction (the piezoelectric element arrangement direction in the 1D array) of the ultrasonic transducer. Note that the embodiment includes a case where a plurality of piezoelectric elements are divided along the elevation direction Ye and are arranged in a one-dimensional array such as 1.25D, 1.5D, and 1.75D in order to acquire a single ultrasonic image for a scan direction Ys.

In addition, while a convex type ultrasonic transducer has been described by way of example, the disclosure can be applied to a linear type transducer. In a case where the ultrasonic transducer is a linear transducer, its scan region has a rectangular shape (such as an oblong rectangular shape and a square shape).

In addition, although the piezoelectric element that emits ultrasonic waves and converts the ultrasonic waves incident from the outside into an echo signal has been described by way of example in the aforementioned embodiment, the disclosure is not limited thereto. The disclosure may be applied to any element manufactured using a micro electro mechanical system (MEMS) such as a capacitive micromachined ultrasonic transducer (C-MUT) or a piezoelectric micromachined ultrasonic transducer (P-MUT).

In addition, the disclosure may be applied to a narrow-diameter ultrasonic probe that performs scanning by mechanically rotating the transducer without an optical system as the ultrasonic endoscope. The ultrasonic probe is inserted into biliary tract, bile duct, pancreatic duct, trachea, bronchi, urethra, or ureter, and is used to observe surrounding organs (such as pancrea, lung, prostate, bladder, or lymph node).

According to the present disclosure, it is possible to miniaturize the casing for housing the ultrasonic transducer.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic endoscope comprising:
   an ultrasonic transducer including an ultrasonic wave transmission/reception surface configured to irradiate a subject with an ultrasonic wave and receive an ultrasonic echo reflected from the subject;
   a cable including one end electrically connected to the ultrasonic transducer and another end electrically connected to a board connected to an ultrasonic observation device that transmits or receives a signal to or from the ultrasonic transducer;
   a relay board configured to relay an electrical connection between the ultrasonic transducer and the one end of the cable; and
   an exterior casing formed of a single type of resin having an insulation property, the casing having:
      a first opening defining a cavity having at least first and second walls, the ultrasonic wave transmission/reception surface of the ultrasonic transducer is exposed from the opening and the relay board is disposed in the cavity, the cavity having:
         the first wall on a proximal side of the casing, the first wall having a second opening through which the cable extends, and
         the second wall opposing the first opening through the cavity, wherein the second wall directly abutting on at least a side surface of the relay board.

2. The ultrasonic endoscope according to claim 1, wherein a protrusion is formed on a surface of one of the ultrasonic transducer and the casing, and
another of the ultrasonic transducer and the casing is provided with a hole configured to house the protrusion.

3. The ultrasonic endoscope according to claim 1, wherein a plurality of piezoelectric elements are arranged along a curved surface of the ultrasonic transducer.

4. The ultrasonic endoscope according to claim 1, further comprising:
   a wire connected to the ultrasonic transducer,
   wherein the relay board is configured to connect the wire and cable.

5. The ultrasonic endoscope according to claim 4, wherein the wire is a flexible board.

6. The ultrasonic endoscope according to claim 1, wherein at least a portion of the relay board and a distal portion of the cable are encased in the resin of the casing such that there is no cavity between at least the side surface of the relay board and corresponding interior surfaces of the cavity.

7. The ultrasonic endoscope according to claim 1, wherein a distal-most portion of the cable is encased in the resin of the casing.

8. The ultrasonic endoscope according to claim 1, wherein at least a portion of the casing abutting on the ultrasonic transducer.

9. The ultrasonic endoscope according to 1, wherein at least the side surface of the relay board abuts the resin of the casing such that there is no cavity between all side surfaces of the relay board and corresponding interior surfaces of the cavity.

* * * * *